United States Patent [19]

Pepper

[11] Patent Number: 4,488,643
[45] Date of Patent: Dec. 18, 1984

[54] SYRINGE AND NEEDLE DISPOSAL SYSTEM
[75] Inventor: Kenneth V. Pepper, Elkhart Lake, Wis.
[73] Assignee: Bemis Manufacturing Company, Sheboygan Falls, Wis.
[21] Appl. No.: 546,324
[22] Filed: Oct. 28, 1983
[51] Int. Cl.³ .............. B65D 25/00; A61M 5/32; B02C 19/12; B26F 1/02; B26F 3/00
[52] U.S. Cl. .................. 206/366; 206/63.5; 206/370; 206/380; 206/216; 225/93
[58] Field of Search ........... 206/366, 365, 370, 380, 206/63.5, 216; 225/93

[56] References Cited
U.S. PATENT DOCUMENTS

| 357,421 | 2/1887 | Spencer | 206/63.5 |
|---|---|---|---|
| 4,168,777 | 9/1979 | Gaskell et al. | 206/370 |
| 4,315,592 | 2/1982 | Smith | 206/370 |
| 4,318,473 | 3/1982 | Sandel | 206/370 |
| 4,332,323 | 6/1982 | Reenstierna | 206/365 |
| 4,351,434 | 9/1982 | Elisha | 206/63.5 |
| 4,375,849 | 3/1983 | Hanifl | 206/63.5 |
| 4,410,086 | 10/1983 | Simpson | 206/63.5 |

Primary Examiner—William T. Dixson, Jr.
Attorney, Agent, or Firm—Dressler, Goldsmith, Shore, Sutker & Milnamow, Ltd.

[57] ABSTRACT

A disposal system for syringe and needle combinations is provided. The system includes a container which is adapted to receive a lid having a flexible resilient one-way valve adapted to allow insertion of a syringe and-/or needle, while preventing re-emergence of the syringe and/or the needle. The lid further includes a passive bending structure adapted to allow bending of the needle, to render the needle unusable, prior to insertion of the syringe and/or the needle into the disposal system container.

17 Claims, 7 Drawing Figures

U.S. Patent  Dec. 18, 1984  Sheet 1 of 2  4,488,643
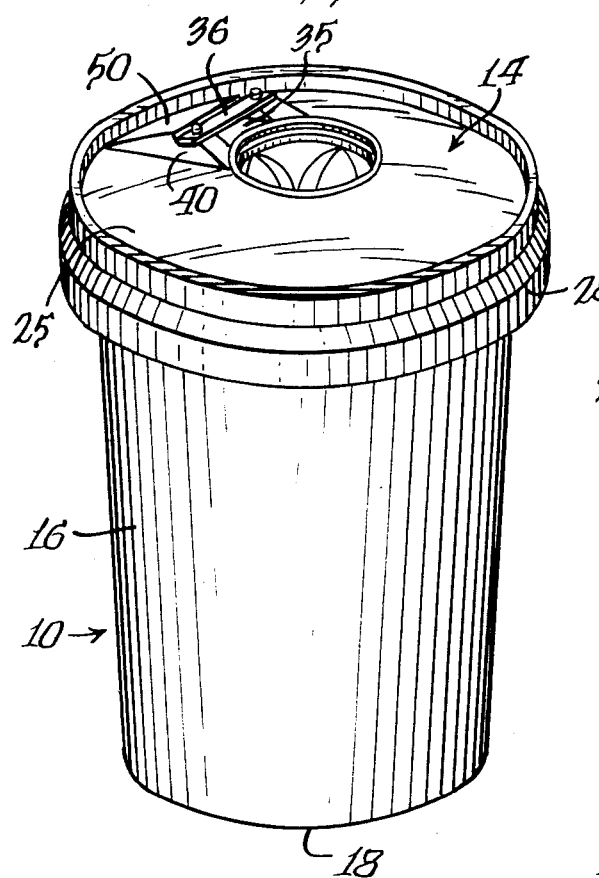
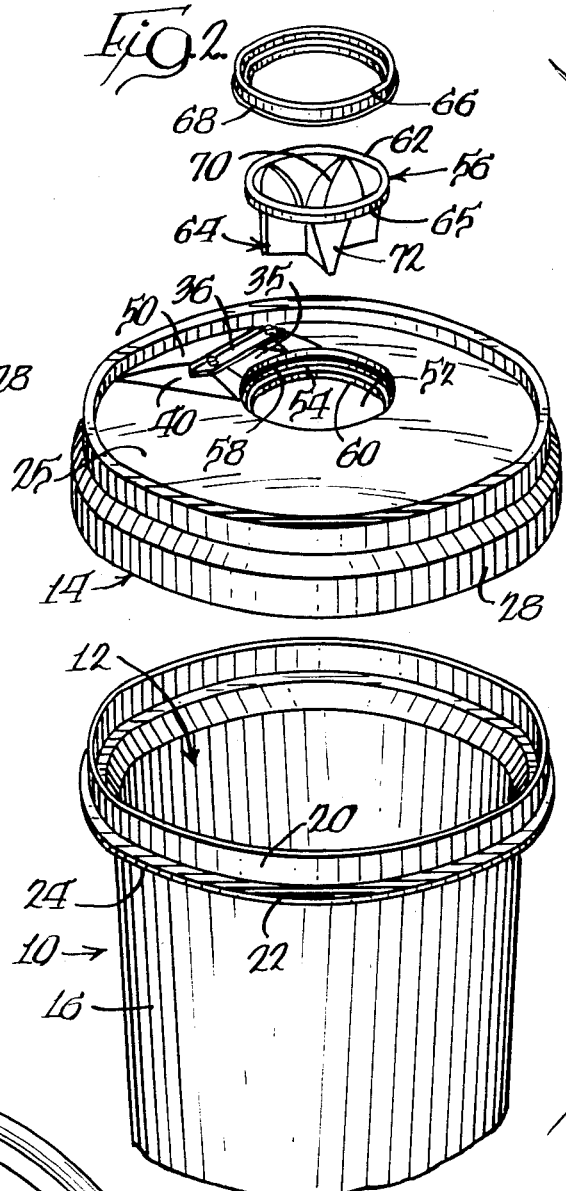
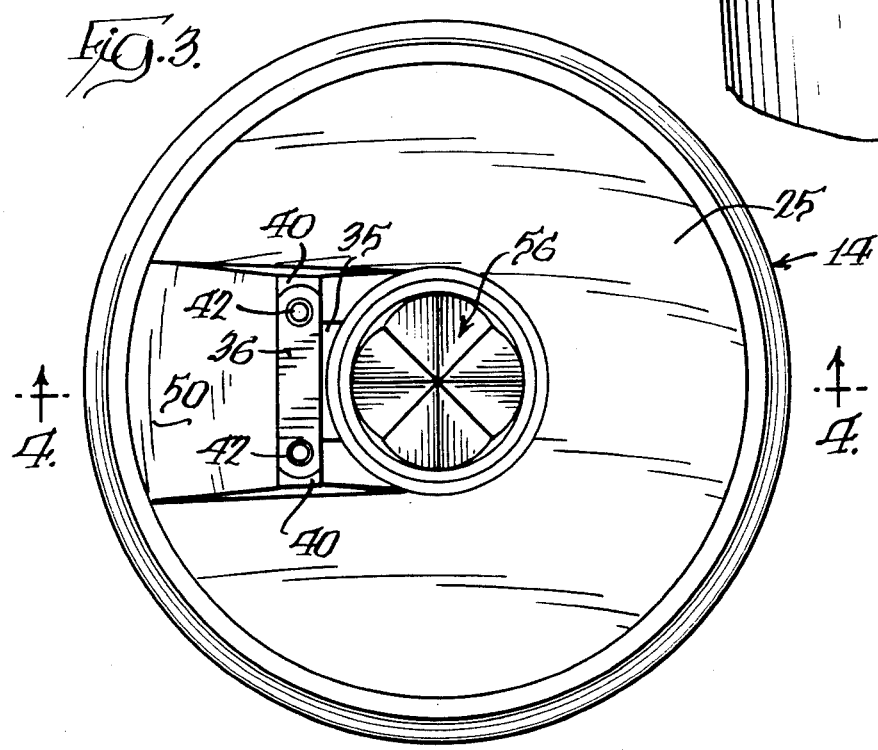

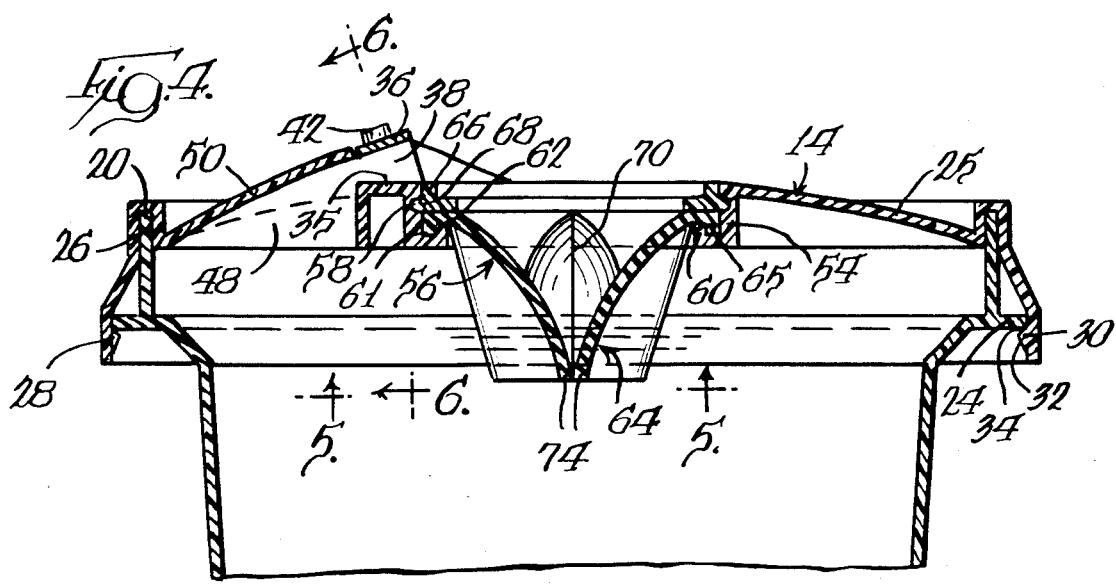
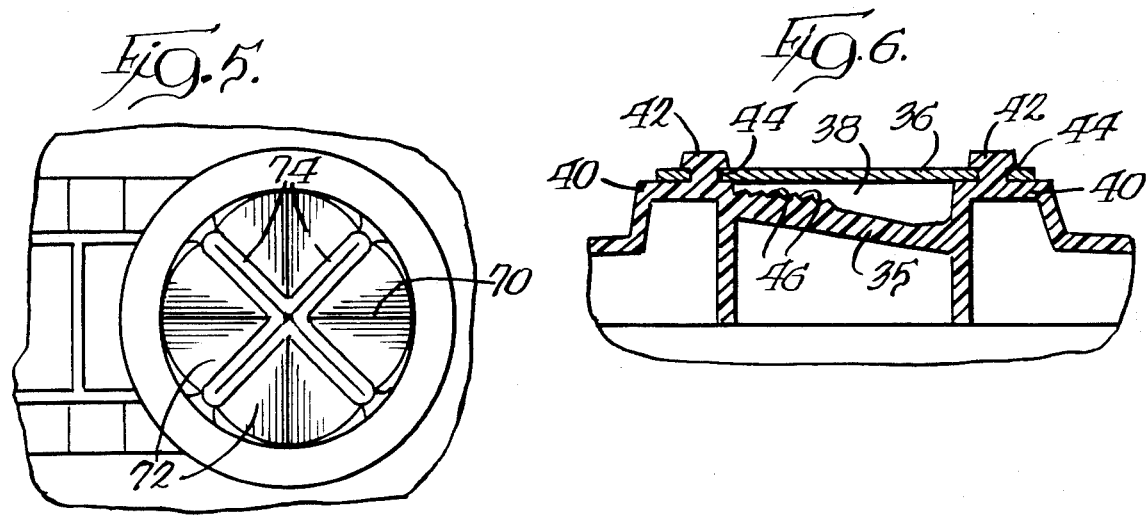
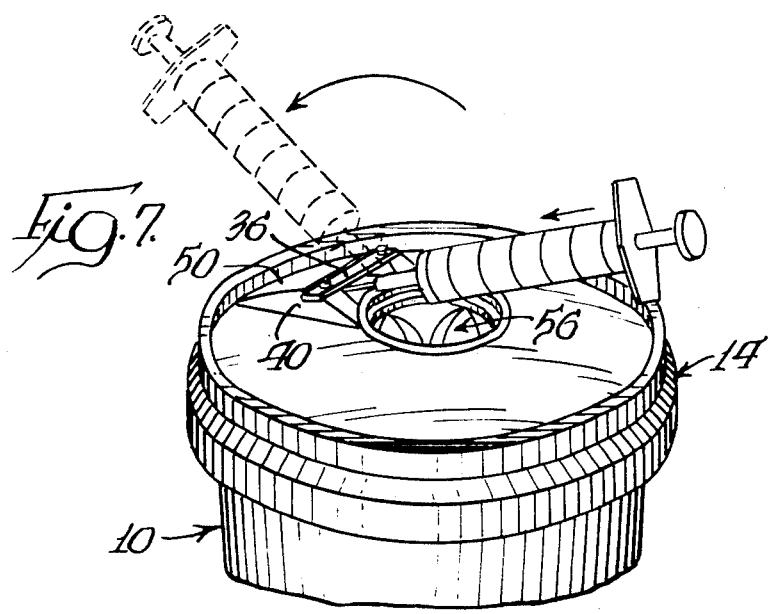

SYRINGE AND NEEDLE DISPOSAL SYSTEM

TECHNICAL FIELD OF THE INVENTION

This invention relates to disposal systems and more particularly to a disposal system for a syringe with a needle including a needle bending structure for rendering the needle of the syringe useless, and a one-way valve closure for receiving the syringe and for preventing re-emergence of the syringe and/or the needle after disposal.

BACKGROUND OF THE INVENTION

The utilization of disposable syringes and needles has given rise to problems concerning the safe disposal of these devices. It is frequently discovered that such syringes and/or needles are the cause of accidental puncture wounds sustained by hospital personnel, or are removed from disposal canisters and fall into the hands of children. These syringes frequently contain a residue of substances which may be harmful, and the needles are frequently contaminated such that contact with the syringe and/or needle may cause the spread of contagious disease or induce infection. In fact, syringe and needle accidents sustained through skin puncture and disease spreading are frequent causes of injury to hospital personnel.

Moreover, several regulatory agencies have begun to adopt strict laws regarding disposal and handling of bio-hazardous waste material, including syringes and needles. These laws require hospital personnel to render the syringes and needles unusable before being discarded, while some also require syringes and needles to be segregated from other waste and placed in rigid containers immediately after use. Furthermore, destruction of the needle renders the combination useless to those who may misuse drugs or who might otherwise acquire used syringes and needles.

Various devices have been proposed for rendering needles unusable and for subsequent disposal of the syringes and needles. One such device includes a rectangular cardboard container having walls reinforced with several layers of cardboard, an aperture and a flexible aperture cover.

One such a disposal system is a rectangular canister having cardboard outer walls reinforced with several layers of cardboard material and having an aperture covered by a combination of foam and plastic. The aperture also includes some mechanism for bending a needle, such as a slot formed in the cardboard and reinforced with a metallic material associated with the aperture to allow the needle to be rendered useless before disposal of the needle and/or syringe.

A disadvantage associated with this type of disposal system includes the lack of an effective closure about the aperture portion, thereby possibly permitting unwanted discharge of the syringe and/or needle after disposal into the canister. This type of disposal system also lacks an effective gripping structure to grip the needle for safer more positive bending thereof. A further disadvantage is the inability to effectively autoclave or sterilize the disposal canister and its contents prior to disposing of the entire system, due to the canisters cardboard construction. The construction of reinforced cardboard walls is unsatisfactory for the additional reasons of undesirable complexity and expense, as well as for the lack of puncture resistance. Further, such unitary, one-piece systems cannot be economically stored, such as by stacking.

Another type of disposal system includes a non-reinforced cardboard container having an opening therethrough for insertion of a syringe and/or needle. This type of disposal system is illustrated in U.S. Pat. No. 4,315,592 to Smith; U.S. Pat. No. 4,121,755 to Meseke et al., and U.S. Pat. No. 3,494,536 to Henry.

These disposal systems are formed from knockdown type cardboard boxes and include an opening within one wall. The major disadvantages associated with this device include the inability of the opening to effectively prevent re-emergence of the syringe and/or needle, after insertion into the system, lack of rigidity and strength, the possibility that the containers could leak and be punctured by the needles therein, as well as the inability of the container to be autoclaved. In addition, such systems are not tamper resistant and may allow inadvertent unauthorized access of the contents of the system. Further, this device does not allow the needle to be rendered unusable which is contrary to many state and federal agency guidelines.

A third type of disposal system previously known includes a molded container having an opening therethrough allowing insertion of a syringe and/or needle. These devices are illustrated in U.S. Pat. No. 4,375,849 to Hanifl; U.S. Pat. No. 4,351,434 to Elisha; and U.S. Pat. No. 3,086,674 to Scheuerman. Disadvantages associated with these devices are that they do not provide for bending of the needle, and do not include a structure to close the opening within the the container to prevent re-emergence of the syringe and/or needle after insertion into the disposal system. Further, none of these systems include provisions for rendering a needle unusable prior to inserting the needle into the container of the disposal system.

Several previously known devices relating to one-way valve structures syringe and needle destroyers and plastic containers are illustrated in U.S. Pat. No. 2,803,370 to Lennard; U.S. Pat. No. 2,818,089 to Mayhill; U.S. Pat. No. 2,822,819 to Geeraert; U.S. Pat. No. 3,111,240 to Whitton, Jr.; U.S. Pat. No. 3,330,404 to Brittell; U.S. Pat. No. 3,444,620 to Ciampa; U.S. Pat. No. 3,585,835 to Clement; U.S. Pat. No. 3,899,100 to Rigaud; U.S. Pat. No. 4,255,996 to Choksi et al.; U.S. Pat. No. 4,275,628 to Greenhouse and U.S. Pat. No. 4,315,448 to Ball. While these patents disclose access valves and mechanical syringe and needle destroyers and plastic containers, none of these patents disclose or teach a one-way access valve for use with a two-piece molded syringe and needle disposal system having the structure of the presently disclosed one-way access valve, or a needle bending structure similar to that of the present invention. Further, none of these patents disclose or teach the combination of a one-way access valve and a simple, inexpensive, passive bending structure for use with a two-piece molded syringe and needle disposal system.

Thus, it would be beneficial to provide a syringe and needle disposal system that includes a one-way access valve providing ease of insertion of a syringe and/or needle, while preventing re-emergence of the syringe and/or needle out of the disposal system container. It would also be desirable to include a simple and inexpensive passing bending structure which would allow the needle to be bent and rendered unusable prior to insertion into the disposal system.

It would further be desirable to provide an improved syringe and needle disposal system that may be molded out of inexpensive rigid material, which would resist puncturing and which would remain intact under the high temperatures of autoclaving or sterilization, prior to discarding of the entire disposal system. In addition, the ability to mold a two-piece system would be desirable to allow economic storage of the disposal system, such as by stacking. Further a disposal system which is tamper-resistent and of relatively small dimensions, facilitating on-site placement and use would also be desirable.

SUMMARY OF THE INVENTION

The syringe and needle disposal system incorporating the present invention, among other things, substantially eliminates the disadvantages noted above by providing a disposal receptacle that includes a simple, inexpensive bending structure and a closure associated with the receptacle. The bending structure is a passive structure disposed externally of the receptacle including spaced upper and lower bending surfaces provided to bend and render the needle useless prior to insertion into the receptacle. The closure comprises a one-way valve which is provided to allow easy insertion of a needle and/or a syringe into the disposal receptacle, while effectively preventing re-emergence of the syringe and/or the needle through the valve area.

The disposal container assembly includes a two-piece molded construction comprising a cover or lid and a vessel or container providing stackability of the container and the lid. The system includes cooperating members on the container and the lid portions, to effectively interengage and seal the lid and container together, resisting separation there between. In addition, the rigidly molded, two-piece construction allows effective autoclaving or sterilizing of the disposal system, as well as providing cost savings due to utilization of molded manufacturing techniques. The disposal system is relatively low in cost, is shatterproof and relatively impenetrable, while being relatively small in overall dimension allowing it to be used in a variety of hospital locations.

In an illustrated embodiment of the present invention, a two-piece disposal container assembly is provided for disposal of syringes and/or needles. The disposal container assembly includes an open topped vessel or container portion adapted to receive a cover or lid portion for closing and sealing the open top of the container portion. The lid portion is adapted to be connected to the container portion and includes a bending bar mounted externally thereon, facilitating bending of the needle prior to insertion of the syringe and/or needle through the valve, thus rendering the needle unusable.

The lid portion also includes a valve, mounted therein, which provides one-way action for ease of insertion of the syringe and/or the needle. Construction in this manner allows the disposal container assembly to remain effectively closed, preventing tampering and undesired exposure or re-emergence of the contents thereof.

The disposal container system of the present invention reduces the chance of accidental puncture wounds to hospital personnel, while providing a cost effective, easy to use system. Further, the disposal system is of a size which allows location at the patient site, and is tamper and pilfer resistant, while resisting against accidental opening, so as to effectively and safely store the syringe and needle combination within the container portion after insertion.

Numerous other advantages and features of the present invention will become readily apparent from the following description of the invention and embodiment thereof, from the drawings and from the appended claims.

BRIEF DESCRIPTION OF THE DRAWINGS

FIG. 1 is a perspective view of the syringe and needle disposal system of the present invention;

FIG. 2 is an exploded perspective view of the syringe and needle disposal system of FIG. 1 illustrating its construction and showing the valve removed from the lid;

FIG. 3 is on enlarged top view of the lid of the syringe and needle disposal system of FIG. 1 illustrating the valve and bending bar in place thereon;

FIG. 4 is an enlarged cross-sectional view taken generally along the plane 4—4 of FIG. 3, showing the details of the lid and valve construction;

FIG. 5 is an enlarged fragmentary bottom view of the lid in FIG. 3 viewed from plane 5—5 of FIG. 4, illustrating the valve mounted within the lid;

FIG. 6 is an enlarged cross-sectional view taken generally along the plane 6—6 of FIG. 4, showing the details of the channel and bending bar configurations; and FIG. 7 is fragmentary perspective view of the syringe and needle disposal system of FIG. 1, showing the present system being used to bend the needle of a syringe and needle combination.

DESCRIPTION OF THE PREFERRED EMBODIMENT

While this invention is susceptible of embodiment in many different forms, there is shown in the drawing and will herein be described in detail, a preferred embodiment of the invention. It should be understood, however, that the present disclosure is to be considered as an exemplification of the principles of the invention and is not intended to limit the invention to the embodiment illustrated.

The embodiment described in detail below, is included merely to aid in the understanding of the invention and variations may be made by one skilled in the art without departing from the spirit and scope of the invention.

As, illustrated in FIGS. 1 and 2, the disposal system of the present invention comprises a receptacle or container 10 that defines a generally open top 12, and a cover or lid 14 which is adapted to close the generally open top 12. The disposal system is typically used in hospitals or similar environments for rendering the needle of a syringe and needle combination unusable, and thereafter for receiving and storing the used syringe and/or needle in the disposal system container for later discarding.

It may be appreciated that while the disposal system of the present invention is described for use in disposing of syringes and/or needles, the disposal system herein described may have use in a variety of situations calling for disposal of different types of objects. It may further be appreciated that minor modifications of the system may be made to adapt the disposal system for use with other objects, all of which are contemplated by the present disclosure.

The container 10 includes a peripheral and generally circular sidewall 16 and a bottom wall 18. The side wall 16 has an upper edge 20 that defines the open top 12 of the container. The vessel is illustrated as having a generally circular construction. However, it may be appreciated by those skilled in the art that the vessel may have a variety of configurations including, but not limited to, an oval or rectangular shape.

The upper edge 20 of the side wall 16 defines a flange 22. The flange 22 is a continuous outward projection that extends about the upper edge 20 adjacent to the open top 12. The under portion of the flange 22 defines a retention surface 24. In addition to functioning as a retention member, flange 22 functions to keep the container 10 angularly disposed with respect to the ground or a table top when the container is on its side. This helps retain the contents, particularly the liquid contents, of the disposal system therein when the system is inadvertently tipped on its side.

The lid 14 includes an outer surface 25 and has a configuration generally corresponding in shape to the upper edge 20. Lid 14 defines a slot 26 adapted to receive upper edge 20, when the lid is positioned over open top 12. The lid defines a generally flared annular collar portion 28 corresponding in shape and size to the flange 22 on the sidewall 16 of the vessel.

A plurality of lips 30 are formed at equally spaced intervals about the inner surface of collar portion 28. Each lip 30 is adapted to cooperatively interengage with the flange 22 to retain the lid portion 14 on the container 10, resisting separation therebetween and inadvertent discharge of the contents thereof. Other forms of complementary means for securing the lid to the vessel may be adapted for use in the present disposal container assembly, including but not limited to, a continuous lip formed about collar portion 28 of lid 14.

As illustrated in FIG. 4, the lips 30 include a camming surface 32 angularly inwardly depending toward the center of the lid 14 and a second retention surface 34 defined by the upper portion of each lip 30. Attachment of the lid 14 to the side wall 16 of the container is accomplished through cooperative interengagement of the camming surface 32 with the upper portion of flange 22 on the side wall 16 of the container. This engagement, followed by downward movement of the lid 14, allows the lid to move onto flange 22 of container 10.

Further movement of the lid 14 allows the camming surface 32 to pass flange 22, facilitating operative interengagement of the first and second retention surfaces 24 and 34. Operative interengagement of the retention surfaces secures the lid to the upper edge of the vessel preventing undesired separation of the container 10 and lid 14. Upon interengagement of first and second retention surfaces 24, 34, the slot 26 will be in sealing engagement with the upper edge 20 of the container 10 thereby creating a seal between the lid and the container, reducing, the possibility of inadvertent discharge of the contents therefrom.

As best illustrated in FIGS. 3 and 6, the lid 14 includes a passive needle bending structure which allows the user to bend the needle prior to insertion into the disposal system. The bending structure includes upper and lower bending surfaces disposed on outer surface 25, externally of the syringe and needle disposal system. More specifically the lower bending surface comprises a portion 35 of outer surface 25 of lid 14. The upper bending surface comprises a bending bar 36 disposed above the outer surface portion, defining channel 38 therebetween for receiving the needle 35, and facilitating bending thereof. The lid further includes a raised support in the form of two upstanding leg portions 40, each having a projection 42 associated therewith. The bending bar 36 includes two apertures 44 which receive projections 42 allowing the bar to be mounted thereto, spanning leg portions 40.

It may be appreciated by those skilled in the art the bending bar 36 may be mounted to leg portions 40 and secured to lid 14 through a variety of mounting methods. These methods include, but are not limited to, positioning each aperture 44 over a respective projection 42 and deforming the projections such that the bending bar is retained thereon, providing a resilient camming surface over which the bending bar may be fastened, forming each projection 42 through an aperture 44 during molding, or like methods.

As best shown in FIG. 6, the outer surface portion 35 is angularly disposed with respect to bending bar 36 mounted thereover and includes a gripping structure in the form of a plurality of teeth or serrations 46 at one end. Serrations 46 facilitate gripping and retention of the needle within channel 38, during wedging of the needle between angular outer surface portion 35 and the bending bar 36, prior to bending the needle. Upon wedging the needle below bending bar 36, the user lifts the syringe upward, away from container 10, thereby bending the needle against the bending bar rendering it unusable.

As can be seen in FIG. 4, lid 14 further includes an opening 48 in communication with channel 38, immediately adjacent angular outer suface portion 35 and between leg portions 40. The lid also includes an upwardly offset portion 50 substantially overlying opening 48 and helping to define channel 38. Accordingly, when the needle is positioned within channel 38, the needle is disposed below offset portion 50 over said opening 48 as illustrated in FIG. 7. Offset portion 50 effectively provides a guide for the needle when it is inserted within channel 38 and prevents liquid from being sprayed out of container 10, during bending thereof. The offset portion 50 also prevents the needle from being projected outside of container 10. In fact, if the needle is broken during bending, the offset portion 50 directs the broken needle into the container through opening 48.

Lid 14 defines a generally central aperture 52 having an aperture wall 54 facilitating mounting of a valve 56 therein. The aperture wall 54 defines an annular recess 58 therein and an annular upwardly turned collet 60 spaced below the groove and inwardly offset toward the center of aperture 52 to define on annular groove 61.

The valve 56 is preferably formed of resilient deformable material such as rubber, plastic or the like. The valve includes an annular rim 62 and an article receiving member 64 depending therefrom. Annular rim 62 includes an out-turned, downwardly depending edge 65 which fits in groove 61 to facilitate mounting of valve 56 within the aperture 52 of lid 14.

The valve 56 is held within aperture 52 by collet 60, and is retained in its mounted position, having its rim 62 held about the collet, by a collar 66. The collar 66 includes an outwardly extending bead 68 adapted to cooperate with recess 58 formed in the aperture wall. Cooperation in this manner facilitates retention of collar 66 and valve 56 within the aperture 52 of lid 14. When positioned in this manner, the upper portion of valve 56 is retained between collet 60 and collar 66.

The receiving member 64, of the valve 56 includes circumferentially spaced inward fold lines 70, defining a plurality of downwardly depending, deflectable flap portions 72. As shown in FIG. 5, the four fold lines 70 are illustrated defining four flap portions 72. It may be appreciated by those skilled in the art, that more or less than four fold lines and/or flap portions may be used. The fold lines 70 interest at the center of receiving member 64 and are disposed substantially parrallel to the longitudinal axis of the depending receiving member 64 in their fully deformed or deflected condition.

The natural configuration of valve 56, by virtue of its resilient nature and molded form, is illustrated in FIG. 2. In this natural configuration, the receiving member 64 is folded on the fold lines 70, to form the four flaps 72, inwardly directed, such that the flaps converge with the lower most edges 74 of flaps 72 adjacent one another in a side by side, touching relationship (FIG. 5). As can be seen in FIGS. 4 and 5, configuration in this manner has the center most corner of each flap at the end of the inward lines of fold 70, in close proximity to one another, such that flaps 72 are positioned so as to cause receiving member 64 to define an "X" across the center of valve 56.

It is apparent that valve 56 is adapted to act as a one way valve with the receiving member 64 substantially closed by downward and inward disposition of flaps 72 when the valve is in its normal configuration. Termination of valve flaps 72, as described above, lends substantial strength to the valve flaps in relatively resisting movement of the syringe and/or the needle in a direction opposite to that of the direction of insertion (i.e., out of the disposal system). In fact, the shape of receiving member 64 causes the flaps 72 to wedge together when an object such as a syringe and/or needle strikes the lower portion of the receiving member from the interior of canister 10.

The valve is sufficiently flexible to permit distortion to a generally polyonal configuration, wherein the lines of fold 70 are unfolded, and thereby allow a syringe and/or needle to pass through the valve 56 and lid 14, and into the container 10. However, absent passage of a syringe and/or needle through the valve, the valve will return to its normally closed configuration, to prevent syringes and needles from re-emerging back through the valve of the disposal system.

As illustrated in FIG. 7 (having a syringe and needle shown in somewhat enlarged proportion for clarity of illustration) and as previously described hereinbefore, the needle may be wedged within the channel 38, between bending bar 36 and lid surface portion 35, bent, removed from the channel and inserted through one-way valve 56 into the container. After the disposal system is full, the entire system may be autoclaved or otherwise sterilized and disposed of as a unit, to prevent undesired handling of bio-hazardous material.

The vessel and lid portion may be fabricated from a variety of suitable materials. Such suitable materials include, but are not limited to, thermoplastic resins and other such media.

Thus, the syringe and needle disposal system of the present invention provides for cost efficient, convenient, tamper resistant, safe and simple disposal of syringes and needles while preventing re-emergence of the syringe or the needle from the disposal system canister. Further, the system provides a simple passive bending structure which allows the needle to be bent and rendered unusable prior to insertion into the container. In addition, the entire system is autoclavable and disposable.

From the foregoing, it will be observed that numerous variations and modifications may be affected without departing from the true spirit and scope of the novel concept of the invention. It is to be understood that no limitation with the respect to the specific apparatus illustrated herein is intended or should be inferred. It is, of course, intended to cover by the apended claims all such modifications as fall within the scope of the claims.

What is claimed is:

1. A syringe and needle disposal system comprising: disposal receptacle means;

passive bending means associated with said disposal receptacle means, said bending means including upper and lower bending surfaces disposed externally of said disposal receptacle means in a spaced relationship with respect to each other and defining a channel therebetween for receiving a needle to facilitate bending thereof; and aperture means associated with said disposal receptacle means for allowing passage of a syringe and needle into said disposal receptacle means.

2. The syringe and needle disposal system of claim 1, including:

closure means associated with said aperture means for allowing passage of said syringe and needle in one direction into said disposal receptacle means, while relatively resisting passage thereof in a second direction out of said disposal receptacle means.

3. The syringe and needle disposal system of claim 1, wherein:

said disposal receptacle means comprises a container portion defining a generally open top and a lid portion mounted on said container portion and resisting separation therebetween and inadvertent discharge of the contents therefrom;

said lid portion defining said aperture means therein; and wherein said bending means is associated with said lid portion.

4. The syringe and needle disposal system of claim 3, wherein:

said lower bending surface comprises a portion of the outer surface of said lid portion;

said upper bending surface comprises bending bar means disposed above said outer surface portion to define said channel therebetween for receiving said needle and for facilitating bending of the needle against said bending bar means when the needle is displaced at an angle with respect to said bending bar means.

5. The syringe and needle disposal system of claim 4, including:

gripping means associated with said lid portion for retaining said needle within said channel to facilitate bending of the needle.

6. The syringe and needle disposal system of claim 4, including:

raised support means for supporting said bending bar means above said outer surface portion.

7. The syringe and needle disposal system of claim 4, including an opening in said lid portion in communication with said channel and said container portion.

8. The syringe and needle disposal system of claim 7, wherein:

said lid portion includes an upwardly offset portion at least partially overlying said opening in said lid portion and at least partially defining said channel.

9. A syringe and needle disposal system comprising:
a container having bottom wall means and side wall means defining a generally open top;
a lid portion generally corresponding in shape to said open top adapted to be mounted on said container portion and resisting separation therebetween and inadvertent discharge of the contents therefrom, said lid portion having an outer surface and having an aperture therethrough for allowing passage of a syringe and a needle into said container;
a pair of upstanding leg portions associated with said lid portion;
an upper bending member spanning said leg portions and affixed thereto;
a lower bending surface spaced below said upper bending member and defining a channel therebetween for receiving the needle and facilitating bending thereof; and
gripping means associated with said channel for retaining the needle therein to facilitate bending thereof.

10. The syringe and needle disposal system of claim 9, wherein:
said lower bending surface comprises a portion of said outer surface of said lid portion;
said lid portion defines an opening therein, between said upstanding leg portions, adjacent said outer surface portion and communicating with said channel and said container; and
said upper bending member comprises a bending bar mounted across said leg portions against which a needle received in the channel may be forced to effect bending thereof.

11. The syringe and needle disposal system of claim 10, wherein:
said outer surface portion is angularly disposed with respect to said bending bar so that a needle may be wedged within said channel between said bending bar and said outer surface portion.

12. The syringe and needle disposal system of claim 11, wherein:
said gripping means includes a plurality serrations on said angularly disposed outer surface portion to facilitate retention of said needle during wedging thereof between said bending bar and said surface portion.

13. The syringe and needle disposal system of claim 10 wherein:
said lid portion includes an upwardly offset portion substantially overlying said opening in said lid portion and defining said channel such that said needle is disposed below said offset portion when the needle is received within said channel.

14. The syringe and needle disposal system of claim 9, including:
valve means mounted within said aperture for allowing passage of said syringe and/or needle in one direction, into said vessel portion, while relatiely resisting passage in a second direction out of said vessel portion.

15. The syringe and needle disposal system of claim 14, wherein:
said valve means comprises a valve having a plurality of downwardly depending resilient flap portions terminating to allow passage of said syringe and/or needle therethrough, while impeding passage of said syringe and needle in the opposite direction.

16. The syringe and needle disposal system of claim 9, including:
cooperating means on said container portion and said lid portion interengaging to resist separation of said lid portion and said container portion for reducing the possibility of inadvertent discharge of the contents therefrom.

17. The syringe and needle disposal system of claim 9, wherein:
said disposal system is molded from a thermoplastic resin.

* * * * *